United States Patent [19]

Camp

[11] 4,200,093
[45] Apr. 29, 1980

[54] STEAM-AIR INHALATOR

[76] Inventor: Nat Camp, 912 Sunset Ave., Gettysburg, Pa. 17325

[21] Appl. No.: 898,101

[22] Filed: Apr. 20, 1978

[51] Int. Cl.² .......................................... A61M 16/00
[52] U.S. Cl. ......................... 128/200.14; 128/200.18; 128/200.21; 128/203.16
[58] Field of Search ................. 128/173.1, 173.2, 194, 128/193, 192, 186, 173 R, 188; 239/338, 318, 370; 261/DIG. 65, DIG. 76, 62

[56] References Cited

U.S. PATENT DOCUMENTS

| | | | |
|---|---|---|---|
| 788,757 | 5/1905 | Deeks | 128/173 R X |
| 1,042,556 | 10/1912 | Holland et al. | 239/338 |
| 3,045,670 | 7/1962 | Hirtz et al. | 128/192 |
| 3,445,067 | 5/1969 | Sheldall | 239/318 |
| 3,894,537 | 7/1975 | Camp | 128/193 |

FOREIGN PATENT DOCUMENTS 1011397   4/1902  France ..................... 239/338

*Primary Examiner*—Henry J. Recla
*Attorney, Agent, or Firm*—Fidelman, Wolffe & Waldron

[57] ABSTRACT

A steam and air mixing chamber having a downwardly open housing is mounted on top of a steam generator located in a housing containing a water reservoir. A steam nozzle directs a jet of steam against a baffle mounted in the mixing chamber entraining air and forming a mist. Compressed air is directed into the mixing chamber by a venturi tube, thereby sucking in the mist and causing the mixture to flow into a breathing element. The vacuum and thus the vapor and mist temperature are controlled by a shielding means which can be moved to overshadow a portion of venturi tube orifice, thereby diverting some of the airstream leaving the venturi tube.

4 Claims, 8 Drawing Figures

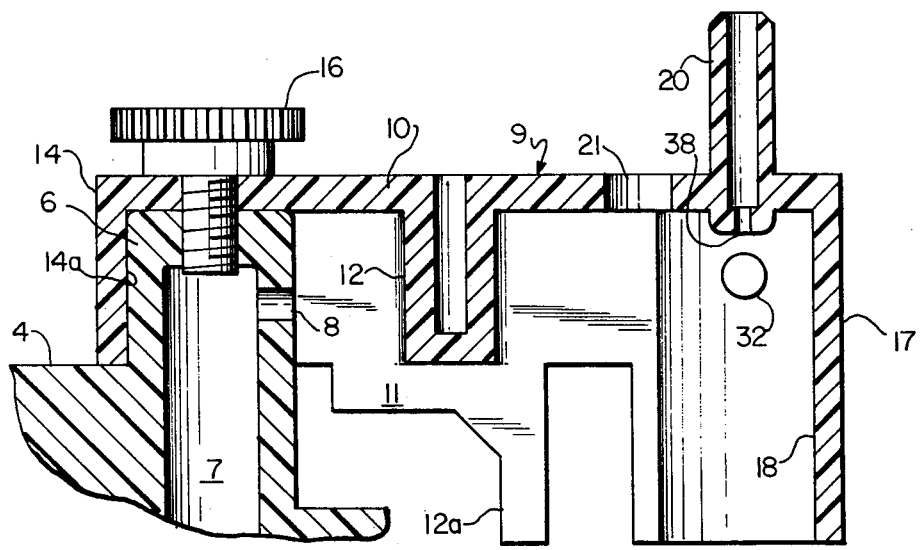
FIG. 3
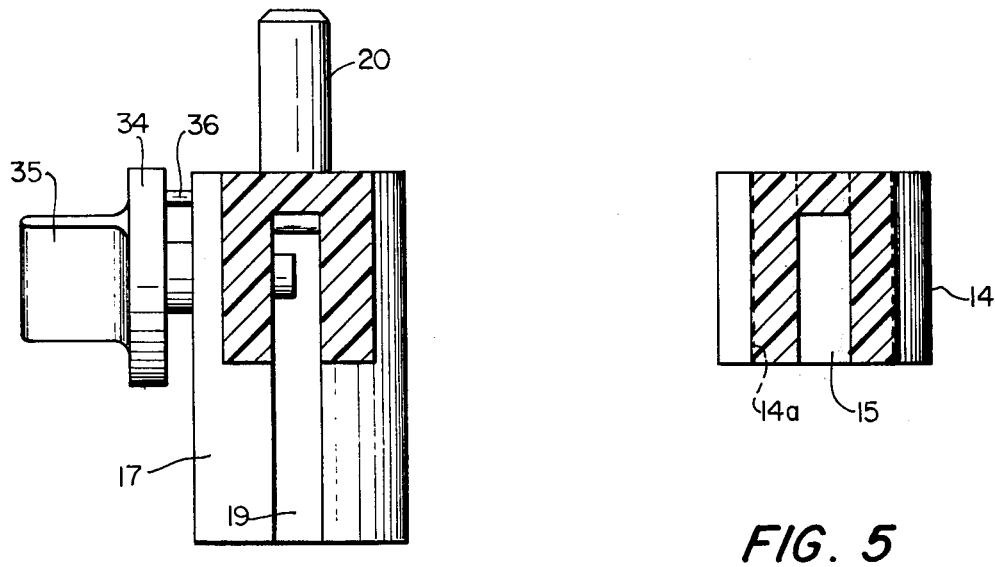
FIG. 4
FIG. 5

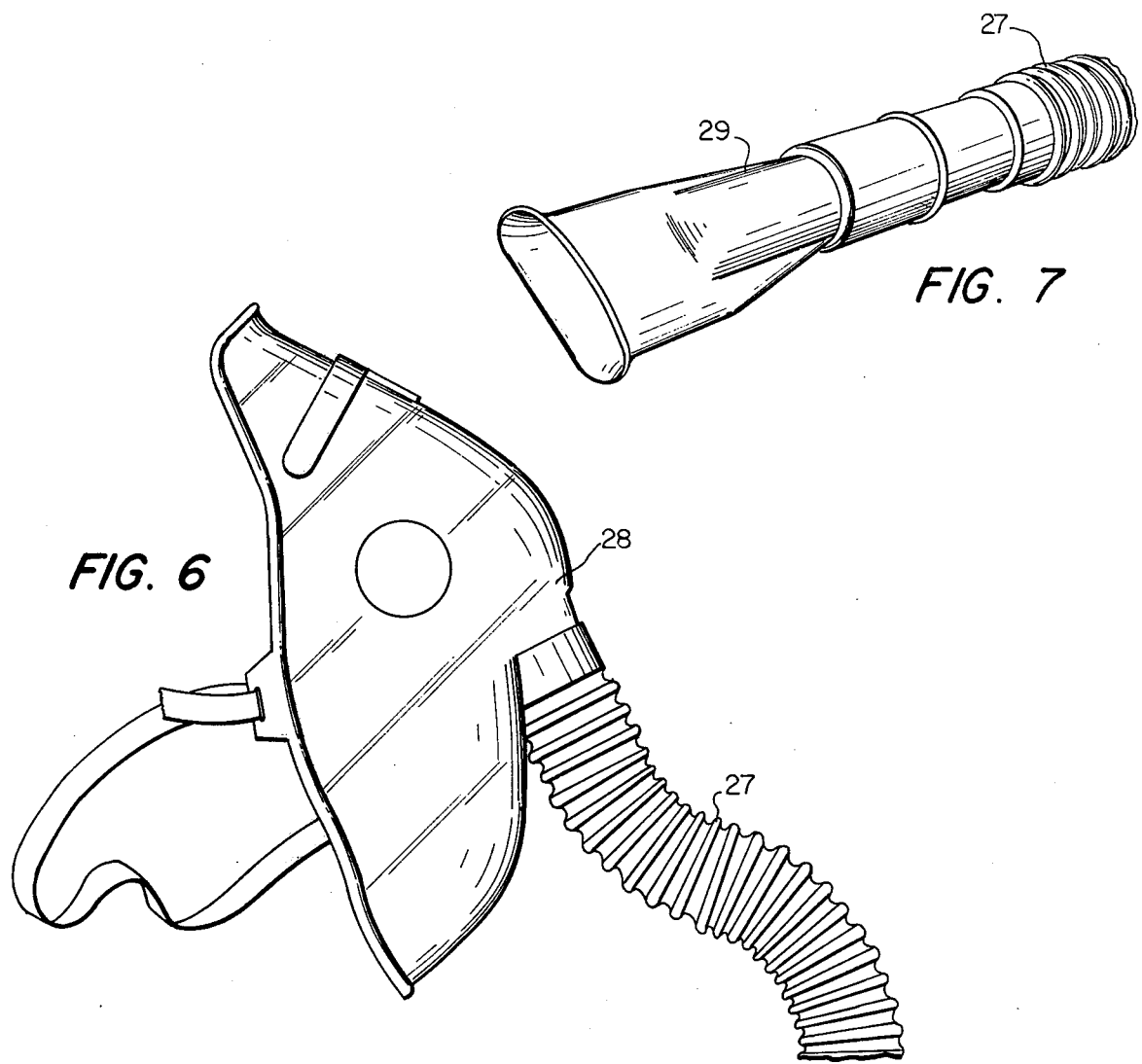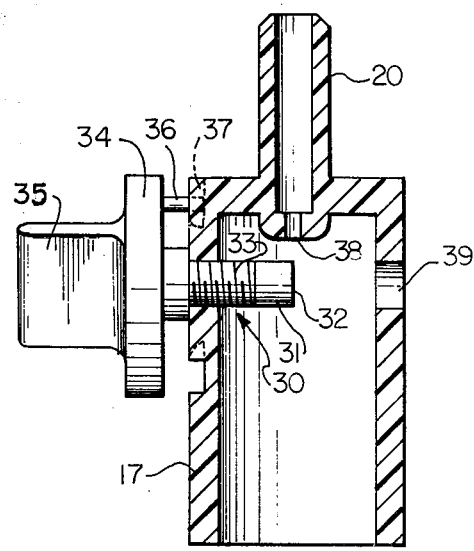

STEAM-AIR INHALATOR

FIELD OF THE INVENTION

This invention relates to a steam-air inhalator device for converting water vapor to a fine mist, to be used, for example, to supply moist air or oxygen to a patient for breathing purposes, and more particularly to a means for controlling the temperature of the moist air and oxygen.

BACKGROUND OF THE INVENTION

Nebulizers are known in which preheated water is driven in a thin stream against a target so as to break up into small particles which mix with the surrounding air in order to moisturize same. Other systems use ultrasonic vibrations to fragmentize the water stream. It is generally desired to make the particle size as small as possible, preferably of 5 microns or less, so as to facilitate penetration of the water particles into the respiratory tract of a patient. However, the mist produced in this manner is not very stable since the water particles are not uniformly dispersed in the airflow and tend to coalesce, thereby forming larger droplets which settle out prematurely in the supply conduit as well as in the respiratory tract itself. The equipment is relatively inefficient, complex and correspondingly expensive, especially for home use; moreover, unless the water is preboiled, sterile conditions are difficult to maintain.

In U.S. Pat. No. 3,894,537, I have described an effective steam-air inhalator which gives very satisfactory results. My copending application Ser. No. 868,569 filed Jan. 10, 1978 is an improvement over this patent in that provision is made for incorporating medication in moist air, or oxygen, or oxygen-rich air and also for returning condensate to the steam generator. Both said patent and application are incorporated herein by reference.

It is a general object of this invention to provide an improved inhalator for producing a stable mist of submicron particles wherein the temperature of said mist can be varied.

A further object is to provide a means to vary the direction of a portion of a pressurized gas stream exiting a venturi tube to vary the vacuum produced in a venturi.

SUMMARY OF THE INVENTION

I realize these objects, in accordance with my present invention, by providing a mixing chamber whose housing has an internal channel partly obstructed by a generally transverse baffle, the housing having an entrance for ambient air communicating with the channel in the vicinity of the baffle. A channel inlet on one side of the baffle has means for directing a jet of stream against the baffle whereby steam in deflected into the surrounding air to form a mist. The surrounding air is constantly aspirated from the ambient atmosphere through the aforementioned entrance with the aid of suction means communicating with the channel on the opposite side of the baffle. An outlet for discharging the mist-laden aspirated air from the channel is provided.

The housing is open at its underside, forming a channel, and the nozzle directs a jet of steam against a baffle located within the channel. Ambient air is drawn into the channel and a superfine mist is formed. At the end of the channel a venturi fitting is located and compressed air, oxygen, or enriched air is passed through a venturi tube. The mist plus additional air is thereby forced into a T connection having a lateral arm attached to a breathing mask or a mouth piece. By laterally deflecting a portion of the gas stream leaving the venturi tube the degree of vacuum created can be changed. As a result, the temperature of the mist entering the breathing mask or mouth piece will likewise change since a higher vacuum will draw more steam-air mixture into the venturi and vice-versa. Means are provided to control the venturi gas stream thereby permitting vapor temperature control by the user.

Copending application Ser. No. 868,569 shows a carrier having volatile medicament thereon which may be inserted through a port in the T connection whereby the mist can be medicated, as for example with antibacterial and decongestant agents. One end of the T connection can extend into the water in the reservoir and serve as a condensate return tube.

BRIEF DESCRIPTION OF THE DRAWING

FIG. 3 is a sectional view of the inhalator.

FIGS. 4 and 5 are sections along lines 4—4 and 5—5 in FIG. 2.

FIG. 6 shows a face mask connected to the inhalator.

FIG. 7 shows a mouth piece for connection to the inhalator.

FIG. 8 is a sectional view of the venturi.

Figure 1:
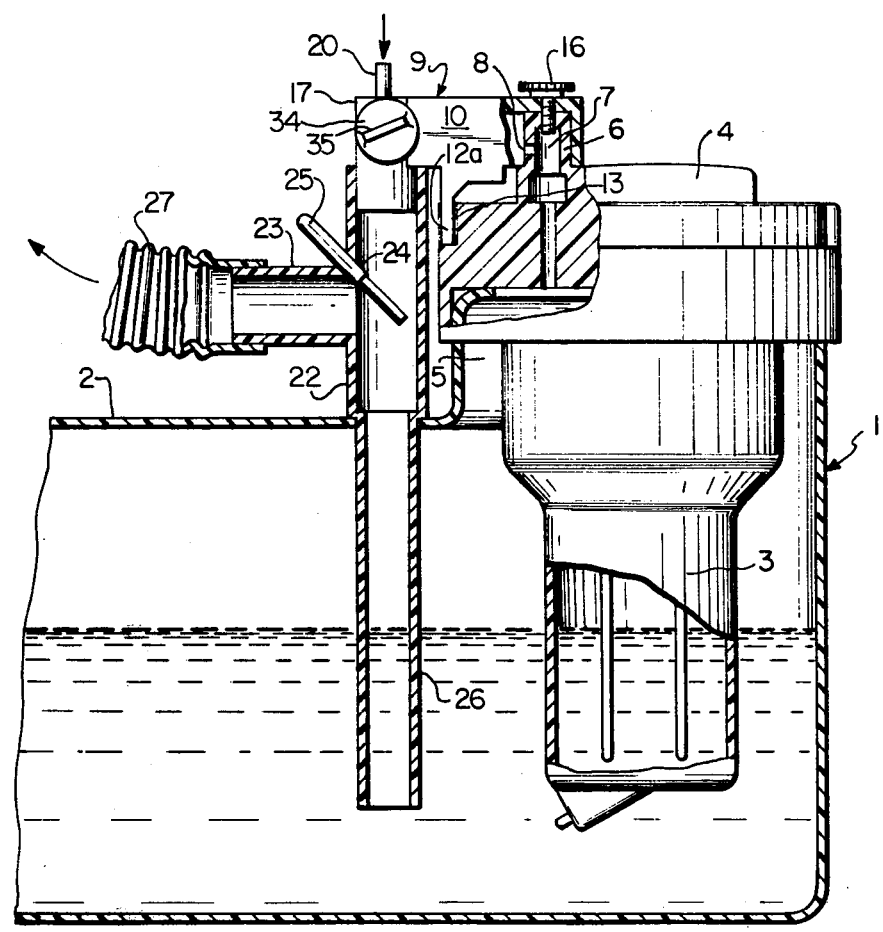
FIG. 1 is an elevational view with parts in section of the inhalator apparatus according to my invention.

The apparatus shown in FIG. 1 comprises a vaporizer having a top surface 2, only a portion of the vaporizer being shown. Advantageously this has the construction of the steam generator disclosed in my prior U.S. Pat. No. 3,743,780. A boiling unit 3 having a top surface 4 and a pair of electrodes encased therein, fits into a raised opening 5 in the top surface of the vaporizer. Steam nozzle 6, which is integrally formed with the top surface 4, has a passageway 7 connected with the boiler for the passage of steam generated therein, and an orifice 8.

Figure 2:
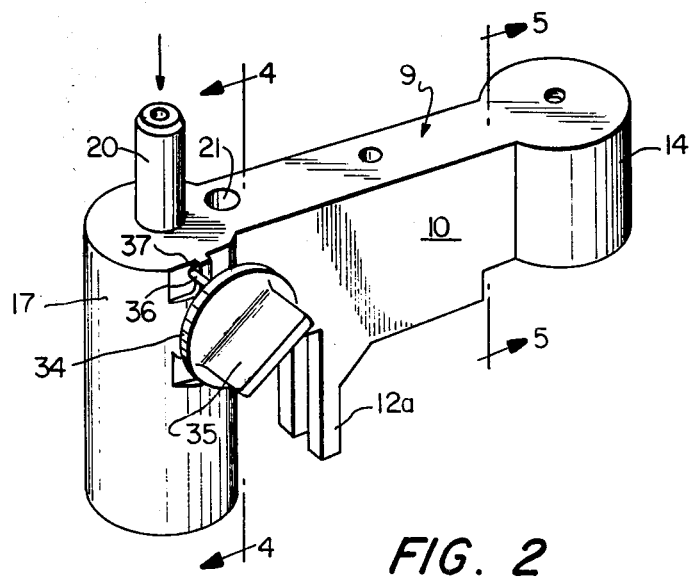
FIG. 2 is a perspective view of the inhalator.

A steam-air mixing chamber 9 has a housing 10 with an internal channel 11 open at the bottom. This channel is partially obstructed by a transverse baffle 12 depending from the closed top of the housing. Depending lugs 12a on the bottom of the housing are adapted to fit into a notch 13 in the top surface of the boiling unit and aids in retaining the mixing chamber in place. One end of the housing 10 is generally cylindrical as shown at 14 having as shown in FIGS. 3 and 5 an internal bore 14a adapted to receive the steam nozzle 6. Bore 14a has a slot 15 in line with orifice 8 in the nozzle. To retain mixing chamber 9 on the vaporizer, screw 16 passes through the mixing chamber at its upper surface at 14 into the top of steam nozzle 6. The end of the mixing chamber opposite 14 likewise is generally cylindrical as shown in FIG. 2 at 17 with a bore 18 having vertical slot 19 therein. Slots 15 and 19 are in line with channel 11, so that a passageway is formed from steam nozzle 6 through passageway 7, orifice 8, slot 15, channel 11, slot 19 and bore 18. Mounted in the upper end of 17 and concentric therewith is verturi tube 20. Pressurized gas, such as for example air, oxygen, oxygen-enriched air, or other gas is passed through 20 into bore 18. It will be seen from FIG. 3 that baffle 12 terminates above the top surface of boiling unit 3 so as to leave free a passage through which ambient air can be aspirated by the steam flowing around the baffle.

Mist laden air from channel 11 with additional ambient air entering through an opening 21 in the top of housing 10 near cylindrical end 17, are aspirated into bore 18 through slot 19 therein. Fitting over cylindrical end 17 at the lower end is a connection consisting of tube 22 having a lateral arm 23, forming a T. Above arm 23, in tube 22 is a port 24 adapted to receive a carrier, such as a rod 25 which is coated with a volatile medicament which can vaporize in the warm stream of mist flowing past it. Various antibacterial and decongestant agents may be employed for use of the invention in treating respiratory ailments, as for example a mixture of camphor, menthol and petrolatum. Rod 25 is coated with a pre-measured dosage by merely dipping the rod into the medicament, which is in the form of a jelly.

The lower end 26 of tube 22 extends through top surface 2 below the level of water in the reservoir and serves to return condensate thereto. Attached to the side arm 23 is flexible tube 27 attached to a conventional face mask 28, (FIG. 6) or to a mouth piece 29 (FIG. 7).

The amount of steam evolving from the generator and the flow rate of pressurized gas should be so chosen as to let the mixture of superfine mist and gas to arrive at the face mask or mouth piece at about body temperature, i.e. approximately 37° C. By way of example and without any intention to limit the invention to the following parameters, I have found that air delivered to the venturi tube 20 at about 2 psi and 200 cu. in. per minute is satisfactory.

The amount of steam entering the breathing element as well as the temperature of the mixture of gas and mist entering side arm 23 may be raised or lowered by reducing or enlarging the size of the channel and accordingly, thereby lower or raise the temperature. Variation of the steam flow may likewise be accomplished by changing the depth of baffle 12. A shallower baffle would allow more steam to pass and thus increase the temperature, while the converse would hold with a longer baffle. Altering the size of opening 21 to vary the amount of ambient air entering the channel through said opening would likewise serve to control the temperature; an increase in the diameter would admit more ambient air and hence lower the temperature, and vice versa.

Returning any condensate formed to the water reservoir enables vaporizer to be used for periods as long as eight hours or more without refilling. In addition, removal of the condensate before it enters the breathing element avoids exposing the patient to the discomfort of having condensate dripping on his body and clothing, so that a long exposure time can be comfortably tolerated.

A preferred method for varying the temperature of the mixture of gas and mist is by partially deflecting the flow of pressurized gas as it leaves the venturi from its normal flow path thereby changing the vacuum produced. The higher the vacuum, the more steam will enter the interior of cylindrical end 17 and conversely. The quantity of compressed gas entering and leaving 17 is not varied, only the direction of flow of a portion is altered at the venturi nozzle, as dscribed below. As a result, the temperature of the mist leaving 17 and entering the breathing apparatus can be readily controlled.

As best shown in FIG. 8, a valve 30 having smooth stem portion 31, a flat end portion 32 and a threaded portion 33, a head 34 and gripper 35 passes through a threaded opening in the wall of 17. The rotation of valve 30 is limited by a pin 36, fastened to 34 as shown, which is adapted to abut a stop 37 in the outer wall portion of 17.

As a result of the pin and stop, the valve can rotate no more than slightly less than one complete revolution. Venturi 20 has a nozzle opening 38 and when the valve is in its furthest extended position as shown in FIG. 8, end 32 is at the midaxis of opening 38. The thread pitch at 33 is such that the retracted position end 32 clears the opening completely. The vertical distance between 32 and 38 is small, but the valve stem does not touch the venturi tube. If desired the end 32 may extend beyond the midaxis of 38 and even go beyond the circumference of the opening in the extended position of 30. However, in this case the pitch of the thread must be such that the retracted position of stem 31 will fully clear opening 38. In the wall of 17 generally opposite 30 is hole 39 which serves to admit additional ambient air into the chamber of cylindrical end 17. It will be appreciated that in all settings of stem 31 the quantity of gas entering the chamber through the venturi tube 20 will be essentially the same.

When the compressed gas stream leaving the orifice is deflected by the stem 31 and stop pin 36 is in contact with boss 37 so that the stem is in its maximum extended position, the vacuum is at its minimum and the inhalator is at its coolest operating condition. Contrariwise, when the stem is at its minimum extended position with stop pin 37 contacting the opposite side of boss 37 the venturi opening is unobstructed and the maximum vacuum is generated. In this position the inhalator is at its warmest operating setting, other conditions being equal.

While the control means for the venturi has been described in connection with the apparatus set forth in my copending application Ser. No. 868,569, it is equally efficacious in the venturi fitting described in my prior U.S. Pat. No. 3,894,537. In general the method described herein for controlling the vacuum of a venturi by a partial direction of the high pressure gas is applicable to venturis as a class.

What is claimed:

1. In a vaporizer comprising a water reservoir, a steam generating means having a steam outlet nozzle and connected to said reservoir, a steam-air mixing chamber in communication with ambient air, the said outlet nozzle connected to one end of said steam-air mixing chamber, whereby the said steam outlet nozzle is adapted to direct a steam jet into said mixing chamber wherein a superfine mist-air mixture is formed by the steam and entering ambient air, a venturi means at the opposite end of the mixing chamber for continuously aspirating the mixture for delivery to a breathing device, the said venturi means comprising a venturi chamber having side walls and first and second ends, a venturi inlet tube connected to said first end of said venturi chamber and adapted to be connected to a source of pressurized gas, said venturi chamber having a diameter greater than said tube, said inlet tube leading into said venturi chamber at said first thereof and having a discharge orifice, the said venturi chamber having an opening in a side wall thereof and communicating with the steam-air mixing chamber whereby a mist-air mixture from the latter can be aspirated into said venturi chamber and means for conveying the mist-air mixture to a breathing device, the improvement comprising; a threaded bore in the venturi chamber wall at a location adjacent the venturi tube orifice, a stem having an outer threaded portion, an inner unthreaded portion, and an inner end, said stem being threaded through the bore with the inner stem portion extending beyond the venturi chamber wall into the venturi chamber and through a projected flow path of the venturi tube orifice, the said inner end being adjacent the venturi tube orifice, whereby rotational movement of the stem serves to move the inner stem end translationally to cover and uncover at least a substantial portion of the projected flow path from the venturi tube orifice, thereby varying the vacuum produced by the venturi, finger gripping means fastened to the other portion of the stem beyond the venturi chamber for rotating the stem and stop means for limiting the rotation of the stem.

2. The vaporizer of claim 1, comprising in addition a port in said mist-air conveying means, a support carrying a volatile medicament extending through said port into the mist-air conveying means, whereby medication is released into said stream.

3. In the vaporizer and improvement of claim 1 wherein the stop means limit the rotation of the stem to substantially one revolution.

4. In the vaporizer and improvement of claim 3 wherein the stop means comprises a pin on the finger gripping means coacting with a boss on in the venturi chamber wall.

* * * * *